US010595720B2

(12) United States Patent
Horne et al.

(10) Patent No.: US 10,595,720 B2
(45) Date of Patent: Mar. 24, 2020

(54) USER INTERFACE FOR ACQUISITION, DISPLAY AND ANALYSIS OF OPHTHALMIC DIAGNOSTIC DATA

(71) Applicant: Carl Zeiss Meditec, Inc., Dublin, CA (US)

(72) Inventors: Melissa R. Horne, Livermore, CA (US); Christine N. Ritter, Alamo, CA (US); Suzanne M. Thompson, San Francisco, CA (US); Raphaël Guilleminot, Brooklyn, NY (US); Jayson Arthur McCauliff, San Francisco, CA (US)

(73) Assignee: CARL ZEISS MEDITEC, INC., Dublin, CA (US)

( * ) Notice: Subject to any disclaimer, the term of this patent is extended or adjusted under 35 U.S.C. 154(b) by 0 days.

(21) Appl. No.: 15/880,147

(22) Filed: Jan. 25, 2018

(65) Prior Publication Data
US 2018/0228365 A1     Aug. 16, 2018

Related U.S. Application Data

(63) Continuation of application No. 15/187,244, filed on Jun. 20, 2016, now Pat. No. 9,907,465, which is a
(Continued)

(51) Int. Cl.
*A61B 3/14* (2006.01)
*A61B 3/10* (2006.01)
(Continued)

(52) U.S. Cl.
CPC .......... *A61B 3/0033* (2013.01); *A61B 3/0025* (2013.01); *A61B 3/0058* (2013.01);
(Continued)

(58) Field of Classification Search
CPC .......... A61B 3/14; A61B 3/0025; A61B 3/12; A61B 3/102; A61B 3/0058
(Continued)

(56) References Cited

U.S. PATENT DOCUMENTS

| 5,321,501 A | 6/1994 | Swanson et al. |
| 6,266,452 B1 | 7/2001 | McGuire |

(Continued)

FOREIGN PATENT DOCUMENTS

| CN | 101032423 A | 9/2007 |
| EP | 2505127 A2 | 10/2012 |
| WO | 2013/022986 A1 | 2/2013 |

OTHER PUBLICATIONS

Ajtony et al., "Relationship between Visual Field Sensitivity and Retinal Nerve Fiber Layer Thickness as Measured by Optical Coherence Tomography", Investigative Ophthalmology & Visual Science, vol. 48, No. 1, Jan. 2007, pp. 258-263.
(Continued)

*Primary Examiner* — Mohammed A Hasan
(74) *Attorney, Agent, or Firm* — Morrison & Foerster LLP (57) ABSTRACT

Improvements to user interfaces for ophthalmic imaging systems, in particular Optical Coherence Tomography (OCT) systems are described to improve how diagnostic data are displayed, analyzed and presented to the user. The improvements include user customization of display and reports, protocol driven work flow, bookmarking of particular B-scans, accessing information from a reference library, customized normative databases, and ordering of follow-up scans directly from a review screen. A further aspect is the ability to optimize the contrast and quality of displayed B-scans using a single control parameter. Virtual real time
(Continued)

z-tracking is described that maintains displayed data in the same depth location regardless of motion.

8 Claims, 8 Drawing Sheets

Related U.S. Application Data continuation of application No. 14/199,874, filed on Mar. 6, 2014, now Pat. No. 9,420,945.

(60) Provisional application No. 61/785,347, filed on Mar. 14, 2013.

(51) Int. Cl.
| | |
|---|---|
| A61B 3/00 | (2006.01) |
| G06F 19/00 | (2018.01) |
| G16H 40/63 | (2018.01) |
| G06F 3/0481 | (2013.01) |
| G06F 3/0484 | (2013.01) |
| G06F 3/0482 | (2013.01) |
| G06F 3/0486 | (2013.01) |

(52) U.S. Cl.
CPC .......... *A61B 3/102* (2013.01); *G06F 3/0482* (2013.01); *G06F 3/0486* (2013.01); *G06F 3/04817* (2013.01); *G06F 3/04842* (2013.01); *G16H 40/63* (2018.01)

(58) Field of Classification Search
USPC ...................................................... 351/206
See application file for complete search history.

(56) References Cited

U.S. PATENT DOCUMENTS

| | | | |
|---|---|---|---|
| 6,542,153 B1 | 4/2003 | Liu | |
| 6,546,272 B1 | 4/2003 | MacKinnon et al. | |
| 6,771,736 B2 | 8/2004 | Sabol et al. | |
| 6,934,698 B2 | 8/2005 | Judd et al. | |
| 7,015,907 B2 | 3/2006 | Tek et al. | |
| 7,020,313 B2 | 3/2006 | Declerck et al. | |
| 7,050,615 B2 | 5/2006 | Avinash et al. | |
| 7,084,128 B2 | 8/2006 | Yerxa et al. | |
| 7,301,644 B2 | 11/2007 | Knighton et al. | |
| 7,347,548 B2 | 3/2008 | Huang et al. | |
| 7,401,921 B2 | 7/2008 | Baker et al. | |
| 7,566,128 B2 | 7/2009 | Tsukada et al. | |
| 7,641,338 B2 | 1/2010 | Fukuma et al. | |
| 7,668,342 B2 | 2/2010 | Everett et al. | |
| 7,768,652 B2 | 8/2010 | Everett | |
| 7,782,464 B2 | 8/2010 | Mujat et al. | |
| 8,045,176 B2 | 10/2011 | Everett et al. | |
| 8,223,143 B2 | 7/2012 | Dastmalchi et al. | |
| 8,332,016 B2 | 12/2012 | Stetson | |
| 8,894,207 B2 | 11/2014 | Hee et al. | |
| 8,931,904 B2 | 1/2015 | Torii | |
| 8,944,597 B2* | 2/2015 | Meyer ................. | A61B 3/14 351/200 |
| 9,033,510 B2 | 5/2015 | Narasimha-Iyer et al. | |
| 9,420,945 B2 | 8/2016 | Coelho et al. | |
| 9,483,866 B2 | 11/2016 | Stetson | |
| 2003/0164860 A1 | 9/2003 | Shen et al. | |
| 2004/0027359 A1 | 2/2004 | Aharon et al. | |
| 2004/0161144 A1 | 8/2004 | Barth | |
| 2005/0238253 A1 | 10/2005 | Behrenbruch et al. | |
| 2006/0030768 A1 | 2/2006 | Ramamurthy et al. | |
| 2006/0119858 A1 | 6/2006 | Knighton et al. | |
| 2006/0184014 A1 | 8/2006 | Pfeiler | |
| 2006/0187462 A1 | 8/2006 | Srinivasan et al. | |
| 2007/0025642 A1 | 2/2007 | Buckland et al. | |
| 2007/0070295 A1 | 3/2007 | Tsukada et al. | |
| 2007/0115481 A1 | 5/2007 | Toth et al. | |
| 2007/0216909 A1 | 9/2007 | Everett et al. | |
| 2007/0222946 A1 | 9/2007 | Fukuma et al. | |
| 2007/0291277 A1 | 12/2007 | Everett et al. | |
| 2008/0100612 A1* | 5/2008 | Dastmalchi ............ | A61B 3/102 345/418 |
| 2009/0244485 A1 | 10/2009 | Walsh et al. | |
| 2010/0073633 A1 | 3/2010 | Uchida et al. | |
| 2010/0079580 A1 | 4/2010 | Waring, IV | |
| 2010/0128943 A1 | 5/2010 | Matsue et al. | |
| 2011/0109631 A1 | 5/2011 | Kunert et al. | |
| 2011/0299034 A1 | 12/2011 | Walsh et al. | |
| 2012/0249769 A1 | 10/2012 | Naba et al. | |
| 2012/0249956 A1* | 10/2012 | Narasimha-Iyer ..... | A61B 3/102 351/206 |
| 2013/0173750 A1* | 7/2013 | Carnevale ............ | G06F 19/321 709/218 |
| 2013/0181976 A1 | 7/2013 | Dastmalchi et al. | |
| 2013/0188132 A1 | 7/2013 | Meyer et al. | |
| 2013/0322716 A1* | 12/2013 | Wollenweber ......... | A61B 6/037 382/131 |
| 2014/0218363 A1 | 8/2014 | Dastmalchi et al. | |
| 2014/0293222 A1 | 10/2014 | Coelho et al. | |

OTHER PUBLICATIONS

Bashkansky et al., "Statistics and Reduction of Speckle in Optical Coherence Tomography", Optics Letters, vol. 25, No. 8, Apr. 15, 2000, pp. 545-547.

Bengtsson et al., "A New Generation of Algorithms for Computerized Threshold Perimetry, SITA", Acta Ophthalmologica Scandinavica, vol. 75, 1997, pp. 368-375.

Budenz et al., "Sensitivity and Specificity of the Stratus OCT for Perimetric Glaucoma", Ophthalmology, vol. 112, No. 1, Jan. 2005, pp. 3-9.

Budenz et al., "Reproducibility of Retinal Nerve Fiber Thickness Measurements using the Stratus OCT in Normal and Glaucomatous Eyes", Investigative Ophthalmology & Visual Science, vol. 46, No. 7, Jul. 2005, pp. 2440-2443.

Carpineto et al., "Custom Measurement of Retinal Nerve Fiber Layer Thickness using Stratus OCT in Normal Eyes", European Journal of Ophthalmology vol. 15, No. 3, 2005, pp. 360-366.

Chang et al., "New Developments in Optical Coherence Tomography for Glaucoma", Current Opinion in Ophthalmology, vol. 19, 2008, pp. 127-135.

Choma et al., "Sensitivity Advantage of Swept Source and Fourier Domain Optical Coherence Tomography", Optics Express, vol. 11, No. 18, Sep. 8, 2003, pp. 2183-2189.

De Boer et al., "Improved Signal-to-Noise Ratio in Spectral-Domain Compared with Time-Domain Optical Coherence Tomography", Optics Letters, vol. 28, No. 21, Nov. 1, 2003, pp. 2067-2069.

El Beltagi et al., "Retinal Nerve Fiber Layer Thickness Measured with Optical Coherence Tomography is Related to Visual Function in Glaucomatous Eyes", Ophthalmology, vol. 110, No. 11, Nov. 2003, pp. 2185-2191.

Final Office Action received for U.S. Appl. No. 11/978,184, dated Jan. 10, 2012, 23 pages.

Final Office Action received for U.S. Appl. No. 13/549,370, dated Jan. 6, 2014, 14 pages.

Final Office Action received for U.S. Appl. No. 14/199,874, dated Jan. 4, 2016, 9 pages.

Frangi et al., "Model-Based Quantitation of 3-D Magnetic Resonance Angiographic Images", IEEE Transactions on Medical Imaging, vol. 18, No. 10, Oct. 1999, pp. 946-956.

Frangi et al., "Multiscale Vessel Enhancement Filtering", Lecture Notes in Computer Science, vol. 1496, 1998, 8 pages.

Gardiner et al., "Evaluation of the Structure-Function Relationship in Glaucoma", Investigative Ophthalmology & Visual Science, vol. 46, No. 10, Oct. 2005, pp. 3712-3717.

Gerig et al., "Nonlinear Anisotropic Filtering of MRI Data", IEEE Transactions on Medical Imaging, vol. 11, No. 2, Jun. 1992, pp. 221-232.

(56) References Cited

OTHER PUBLICATIONS

Haeker et al., "Use of Varying Constraints in Optimal 3-D Graph Search for Segmentation of Macular Optical Coherence Tomography Images", Med Image Comput Comput Assist Interv, vol. 10, Part-1, 2007, pp. 244-251.
Harwerth et al., "Linking Structure and Function in Glaucoma", Progress in Retinal and Eye Research, 2010, pp. 1-23.
Häusler et al., "Coherence Radar and 'Spectral Radar'—New Tools for Dermatological Diagnosis", Journal of Biomedical Optics, vol. 3, No. 1, Jan. 1998, pp. 21-31.
Hitzenberger et al., "Three-Dimensional Imaging of the Human Retina by High-Speed Optical Coherence Tomography", Optics Express, vol. 11, No. 21, Oct. 20, 2003, pp. 2753-2761.
Hougaard et al., "Glaucoma Detection by Stratus OCT", Journal of Glaucoma, vol. 16, No. 3, May 2007, pp. 302-306.
Huang et al., "Optical Coherence Tomography", Science, vol. 254, Nov. 2, 1991, pp. 1178-1181.
Ishikawa et al., "Macular Segmentation with Optical Coherence Tomography", Investigative Ophthalmology & Visual Science, vol. 46, No. 6, Jun. 2005, pp. 2012-2017.
Jiao et al., "Simultaneous Acquisition of Sectional and Fundus Ophthalmic Images with Spectral-Domain Optical Coherence Tomography", Optics Express, vol. 13, No. 2, Jan. 24, 2005, pp. 444-452.
Lee et al., "In Vivo Optical Frequency Domain Imaging of Human Retina and Choroid", Optics Express, vol. 14, No. 10, May 15, 2006, pp. 4403-4411.
Leitgeb et al., "Performance of Fourier Domain vs. Time Domain Optical Coherence Tomography", Optics Express, vol. 11, No. 8, Apr. 21, 2003, pp. 889-894.
Leitgeb et al., "Ultrahigh Resolution Fourier Domain Optical Coherence Tomography", Optics Express, vol. 12, No. 10, May 17, 2004, pp. 2156-2165.
Leung et al., "Comparative Study of Retinal Nerve Fiber Layer Measurement by StratusOCT and GDx VCC, II: Structure/Function Regression Analysis in Glaucoma", Investigative Ophthalmology & Visual Science, vol. 46, No. 10, Oct. 2005, pp. 3702-3711.
Maintz et al., "A Survey of Medical Image Registration", Medical Image Analysis, vol. 2, No. 1, 1998, pp. 1-36.
Maurer et al., "A Review of Medical Image Registration", Vanderbilt University, Nashville, Tennessee 37235, Jan. 28, 1993, pp. 1-49.
Nassif et al., "In Vivo Human Retinal Imaging by Ultrahigh-Speed Spectral Domain Optical Coherence Tomography", Optics Letters, vol. 29, No. 5, Mar. 1, 2004, pp. 480-482.
Non-Final Office Action received for U.S. Appl. No. 11/978,184, dated Jul. 18, 2011, 17 pages.
Non-Final Office Action received for U.S. Appl. No. 13/549,370, dated Jul. 2, 2013, 12 pages.
Non-Final Office Action received for U.S. Appl. No. 14/199,874, dated Jul. 2, 2015, 10 pages.
Non-Final Office Action received for U.S. Appl. No. 13/740,875, dated Jun. 6, 2014, 11 pages.
Non-Final Office Action received for U.S. Appl. No. 14/245,910, dated Mar. 25, 2016, 13 pages.
Non-Final Office Action received for U.S. Appl. No. 15/187,244, dated May 11, 2017, 8 pages.
Notice of Allowance received for U.S. Appl. No. 13/740,875, dated Oct. 8, 2014, 7 pages.
Notice of Allowance received for U.S. Appl. No. 11/978,184, dated Mar. 20, 2012, 14 pages.
Notice of Allowance received for U.S. Appl. No. 11/978,184, dated May 10, 2012, 4 pages.
Notice of Allowance received for U.S. Appl. No. 14/245,910, dated Jun. 29, 2016, 11 pages.
Notice of Allowance received for U.S. Appl. No. 15/187,244, dated Oct. 30, 2017, 10 pages.
Pal et al., "A Review on Image Segmentation Techniques", Pattern Recognition, vol. 26, No. 9, 1993, pp. 1277-1294.
Paunescu et al., "Reproducibility of Nerve Fiber Thickness, Macular Thickness, and Optic Nerve Head Measurements using StratusOCT", Investigatative Ophthalmology & Visual Science, vol. 45, No. 6, Jun. 2004, pp. 1716-1724.
Perona et al., "Scale-Space and Edge Detection using Anisotropic Diffusion", IEEE Transaction on Pattern Analysis and Machine Intelligence, vol. 12, No. 7, Jul. 1990, pp. 629-639.
Podoleanu et al., "Combined Multiplanar Optical Coherence Tomography and Confocal Scanning Ophthalmoscopy", Journal of Biomedical Optics, vol. 9, No. 1, Jan./Feb. 2004, pp. 86-93.
Podoleanu et al., "Transversal and Longitudinal Images from the Retina of the Living Eye using Low Coherence Reflectometry", Journal of Biomedical Optics, vol. 3, No. 1, Jan. 1998, pp. 12-20.
Sadda et al., "Errors in Retinal Thickness Measurements Obtained by Optical Coherence Tomography", Ophthalmology, vol. 113, No. 2, Feb. 2006, pp. 285-293.
Sato et al., "Correlation Between Retinal Nerve Fibre Layer Thickness and Retinal Sensitivity", Acta Ophthalmologica, vol. 86, 2008, pp. 609-613.
Sato et al., "Three-Dimensional Multi-Scale Line Filter for Segmentation and Visualization of Curvilinear Structures in Medical Images", Medical Image Analysis, vol. 2, No. 2, 1998, pp. 143-168.
Schmitt et al., "Speckle in Optical Coherence Tomography", Journal of Biomedical Optics, vol. 4, No. 1, Jan. 1999, pp. 95-105.
Schuman et al., "Reproducibility of Nerve Fiber Layer Thickness Measurements Using Optical Coherence Tomography", Ophthalmology, vol. 103, No. 11, Nov. 1996, pp. 1889-1898.
Sommer et al., "Clinically Detectable Nerve Fiber Atrophy Precedes the Onset of Glaucomatous Field Loss", Arch Ophthalmol, vol. 109, Jan. 1991, pp. 77-83.
Tan et al., "Detection of Macular Ganglion Cell Loss in Glaucoma by Fourier-Domain Optical Coherence Tomography", Ophthalmology, vol. 116, No. 12, Dec. 2009, pp. 2305-2314.e2.
Vermeer et al., "A Model Based Method for Retinal Blood Vessel Detection", Computers in Biology and Medicine, vol. 34, 2004, pp. 209-219.
Wojtkowski et al., "Three-dimensional Retinal Imaging with High-Speed Ultrahigh-Resolution Optical Coherence Tomography", Ophthalmology, vol. 112, No. 10, Oct. 2005, pp. 1734-1746.
Yanuzzi et al., "Ophthalmic Fundus Imaging: Today and Beyond", American Journal of Opthalmoscopy, vol. 137, No. 3, Mar. 2004, pp. 511-524.
Yu et al., "Speckle Reducing Anisotropic Diffusion", IEEE Transactions on Image Processing, vol. 11, No. 11, Nov. 2002, pp. 1260-1270.
Zana et al., "A Multimodal Registration Algorithm of Eye Fundus Images using Vessels Detection and Hough Transform", IEEE Transactions on Medical Imaging, vol. 18, No. 5, May 1999, pp. 419-428.
Zawadzki et al., "Adaptation of a Support Vector Machine Algorithm for Segmentation and Visualization of Retinal Structures in Volumetric Optical Coherence Tomography Data Sets", Journal of Biomedical Optics, vol. 12, No. 4, Jul./Aug. 2007, pp. 041206-1-041206-8.
Non-Final Office Action received for U.S. Appl. No. 15/289,403, dated Dec. 20, 2016, 10 pages.
Office Action received for Chinese Patent Application No. 2014800145066, dated May 16, 2017, 8 pages (English Translation Only).
Office Action received for Japanese Patent Application No. 2015-562186, dated Jan. 30, 2018, 3 pages (English Translation Only).
Wojtkowski et al., "Ophthalmic Imaging by Spectral Optical Coherence Tomography", American Journal of Ophthalmology, vol. 138, No. 3, Sep. 2004, pp. 412-419.
Corrected Notice of Allowance received for U.S. Appl. No. 14/199,874, dated Apr. 19, 2016, 5 pages.
Non-Final Office Action received for U.S. Appl. No. 15/608,239, dated Nov. 2, 2018, 7 pages.
Notice of Allowance received for U.S. Appl. No. 14/199,874, dated Mar. 22, 2016, 8 pages.
Notice of Allowance received for U.S. Appl. No. 15/608,239, dated Feb. 25, 2019, 8 pages.

(56) References Cited

OTHER PUBLICATIONS

Office Action received for European Patent Application No. 14710265.1, dated Dec. 7, 2018, 5 pages.

* cited by examiner

USER INTERFACE FOR ACQUISITION, DISPLAY AND ANALYSIS OF OPHTHALMIC DIAGNOSTIC DATA

PRIORITY

The present application is a continuation of U.S. patent application Ser. No. 15/187,244, filed Jun. 20, 2016, which is a continuation of U.S. patent application Ser. No. 14/199,874, filed Mar. 6, 2014, now U.S. Pat. No. 9,420,945, which claims priority to U.S. Provisional Application Ser. No. 61/785,347, filed Mar. 14, 2013, the contents of which are hereby incorporated in its entirety by reference.

TECHNICAL FIELD

The present invention relates to ophthalmic diagnostic testing and imaging, and in particular to graphical user interface improvements for acquisition, display and analysis of ophthalmic diagnostic data.

BACKGROUND

The field of ophthalmic diagnostics includes both imaging based or structural techniques and functional approaches to diagnose and monitor various pathologies in the eye. One pathology of interest is glaucoma, an optic neuropathy resulting in characteristic visual field defects. It arises from progressive damage to the optic nerve (ON) and retinal ganglion cells (RGCs) and their axons, the retinal nerve fiber layer (RNFL). Investigating the relationship between development of functional damage in the visual field and structural glaucomatous changes of the RNFL has been the purpose of numerous studies [1-5].

Diagnostic instruments providing quantitative analyses in glaucoma assess either structural or functional aspects of the disease. Optical Coherence Tomography (OCT) is one technique capable of imaging the retina and providing quantitative analysis of RNFL measurements and measuring the optic nerve head. OCT is a noninvasive interferometric technique that provides cross sectional images and thickness measurements of various retinal layers including the RNFL (RNFLT) with high resolution [6] and good reproducibility [7-9]. Standard Automated white-on-white Perimetry (SAP) is the standard for assessing visual function by examination of the visual field. Parametric tests are able to provide quantitative measurements of differential light sensitivity at many test point locations in the visual field, and commercially available statistical analysis packages help clinicians in identifying significant visual field loss [10]. The diagnostic performance of both OCT and SAP in glaucoma as well as the correlation between SAP and OCT measurements has been investigated [11-14].

Clinical studies suggest that these diagnostic tests, used in isolation, provide useful information on the diagnosis and progression of the disease and, used in conjunction, provide supportive and complementing information which could lead to improved accuracy in disease detection and monitoring of progression. However, there is not one single diagnostic test used in isolation that provides adequate diagnostic accuracy and applicability across patient populations and disease dynamic range. It is therefore desirable to collect, display and analyze data from multiple ophthalmic diagnostic devices as is commercially available in the FORUM (Carl Zeiss Meditec, Inc. Dublin, Calif.) software package that allows customers to integrate and store ophthalmic diagnostic data from and analysis from multiple modalities and perform additional analysis on the combined data. It may also be desirable to display data from multiple diagnostic modalities on a single instrument so that the instrument operator can have the most complete picture of the patient for use in guiding the acquisition of data. Although the situation has been described in detail for glaucoma, the need for information from multiple modalities, including structural and functional measurements, which may complement each other and aid in diagnosis and treatment management decisions when reviewed together, is general to the ophthalmic field.

In commercially available ophthalmic diagnostic systems, the instrument operator typically selects from a series of scanning options based on known locations in the eye that may be relevant to a specific pathology. The data is displayed and analyzed in standard formats specified by the instrument manufacturer. As improvements in OCT technology allow for collection of larger volumes of data without appreciable patient motion artifacts, there is more and more data to be analyzed and interpreted. It is desirable to increase automation and interpretation in the display and analysis of these large volumes of data to improve and expand clinical applications of the technology.

SUMMARY

It is an object of the present invention to improve the ways in which OCT and other ophthalmic diagnostic data is displayed, analyzed and presented to the user. In one aspect of the present invention, the user is allowed to create customizable views or reports by dragging and dropping different display elements on the graphical user interface. In another aspect of the invention, the user is provided options to order scans based on protocols for specific pathologies. Further enhancements to the user interface include the ability to bookmark particular B-scans, access information from a reference library, and order follow-up scans directly from a review screen. A further aspect of the present invention is the ability to optimize the contrast and quality of displayed B-scans using a single control parameter. In a further aspect of the invention, a virtual real time z-tracking approach is described that maintains displayed data in the same depth location regardless of motion. This embodiment may have specific application in the use of OCT in surgical systems. In a final aspect of the present invention, an ophthalmic diagnostic instrument in which the user has the ability to collect and perform analysis using a database of data on a normal population that is of interest to them rather than the standard normative database that is provided by the instrument manufacturer.

BRIEF DESCRIPTION OF THE FIGURES

FIGS. 2a and 2b show two examples of user customizable interface screens to drive acquisition, display and analysis of ophthalmic diagnostic data according to an embodiment of the present invention.

FIGS. 3a and 3b show two examples of user customizable report screens to drive acquisition, display and analysis of ophthalmic diagnostic data according to an embodiment of the present invention.

DETAILED DESCRIPTION

Optical Coherence Tomography (OCT) is a technique for performing high-resolution cross-sectional imaging that can provide images of tissue structure on the micron scale in situ and in real time [15]. OCT is a method of interferometry that determines the scattering profile of a sample along the OCT beam. Each scattering profile is called an axial scan, or A-scan. Cross-sectional images (B-scans), and by extension 3D volumes, are built up from many A-scans, with the OCT beam moved to a set of transverse locations on the sample. OCT provides a mechanism for micrometer resolution measurements.

In frequency domain OCT (FD-OCT), the interferometric signal between light from a reference and the back-scattered light from a sample point is recorded in the frequency domain rather than the time domain. After a wavelength calibration, a one-dimensional Fourier transform is taken to obtain an A-line spatial distribution of the object scattering potential. The spectral information discrimination in FD-OCT is typically accomplished by using a dispersive spectrometer in the detection arm in the case of spectral-domain OCT (SD-OCT) or rapidly scanning a swept laser source in the case of swept-source OCT (SS-OCT).

Figure 1:
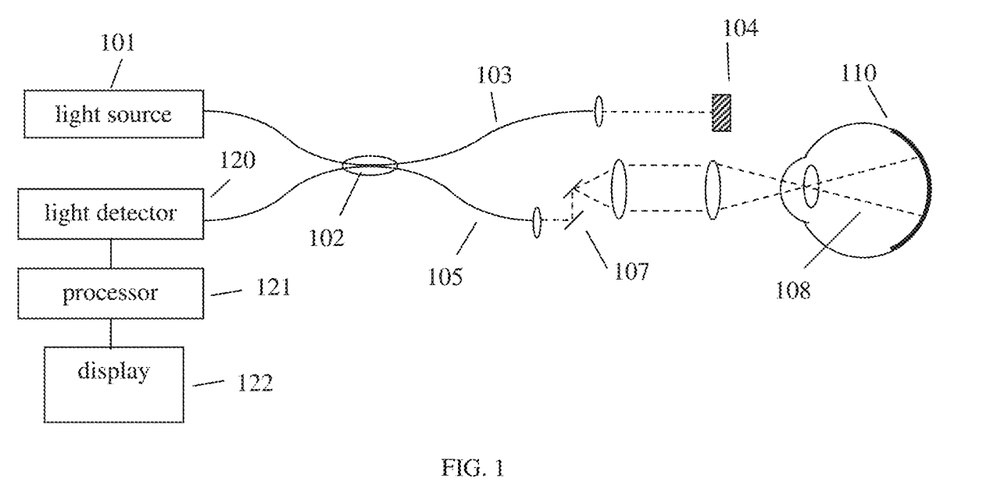
FIG. 1 shows a generalized diagram of an ophthalmic OCT device that can be used in various embodiments of the present invention.

Evaluation of biological materials using OCT was first disclosed in the early 1990's [16]. Frequency domain OCT techniques have been applied to living samples [17]. The frequency domain techniques have significant advantages in speed and signal-to-noise ratio as compared to time domain OCT [18]. The greater speed of modern OCT systems allows the acquisition of larger data sets, including 3D volume images of human tissue. The technology has found widespread use in ophthalmology. A generalized FD-OCT system used to collect 3-D image data suitable for use with the present invention is illustrated in FIG. 1.

A FD-OCT system includes a light source, 101, typical sources including but not limited to broadband light sources with short temporal coherence lengths or swept laser sources [19-20]. Light from source 101 is routed, typically by optical fiber 105, to illuminate the sample 110, a typical sample being tissues at the back of the human eye. The light is scanned, typically with a scanner 107 between the output of the fiber and the sample, so that the beam of light (dashed line 108) is scanned over the area or volume to be imaged. Light scattered from the sample is collected, typically into the same fiber 105 used to route the light for illumination. Reference light derived from the same source 101 travels a separate path, in this case involving fiber 103 and retro-reflector 104. Those skilled in the art recognize that a transmissive reference path can also be used. Collected sample light is combined with reference light, typically in a fiber coupler 102, to form light interference in a detector 120. The output from the detector is supplied to a processor 130. The results can be stored in the processor or displayed on display 140. The processing and storing functions may be localized within the OCT instrument or functions may be performed on an external processing unit to which the collected data is transferred. This unit could be dedicated to data processing or perform other tasks which are quite general and not dedicated to the OCT device.

The interference causes the intensity of the interfered light to vary across the spectrum. The Fourier transform of the interference light reveals the profile of scattering intensities at different path lengths, and therefore scattering as a function of depth (z-direction) in the sample [21]. The profile of scattering as a function of depth is called an axial scan (A-scan). A set of A-scans measured at neighboring locations in the sample produces a cross-sectional image (tomogram or B-scan) of the sample. A collection of B-scans collected at different transverse locations on the sample makes up a data volume or cube.

The sample and reference arms in the interferometer could consist of bulk-optics, fiber-optics or hybrid bulk-optic systems and could have different architectures such as Michelson, Mach-Zehnder or common-path based designs as would be known by those skilled in the art. Light beam as used herein should be interpreted as any carefully directed light path. In time-domain systems, the reference arm needs to have a tunable optical delay to generate interference. Balanced detection systems are typically used in TD-OCT and SS-OCT systems, while spectrometers are used at the detection port for SD-OCT systems. The invention described herein could be applied to any type of OCT system. Various aspects of the invention could apply to other types of ophthalmic diagnostic systems and/or multiple ophthalmic diagnostic systems including but not limited to fundus imaging systems, visual field test devices, and scanning laser polarimeters. The invention relates to acquisition controls, processing and display of ophthalmic diagnostic data that can be done on a particular instrument itself or on a separate computer or workstation to which collected diagnostic data is transferred either manually or over a networked connection. The display provides a graphical user interface for the instrument or operator to interact with the system and resulting data. The instrument user can interact with the interface and provide input in a variety of ways including but not limited to, mouse clicks, touchscreen elements, scroll wheels, buttons, knobs, etc. Various aspects of a user interface design for OCT applications have been described [22]. The invention described herein is directed towards improvements in how the user interface is designed and configured to allow for optimized acquisition, display and analysis of ophthalmic diagnostic data.

Customizable User Interface and Reports

Figure 2A:
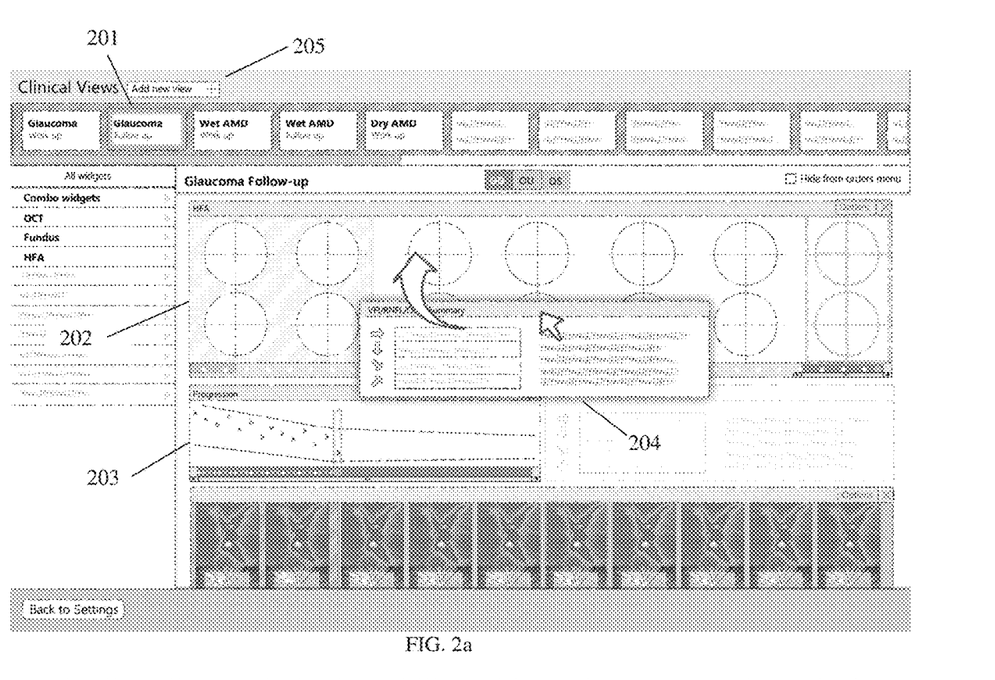
FIG. 2a shows a display for a Glaucoma Follow-up clinical view in which a variety of display elements relevant to glaucoma would be displayed and selected by a user to create a view of one or more sets of ophthalmic diagnostic data.

In one embodiment of the present invention, the user interface provides a fully customizable report/clinical view functionality. The user has the option to create their own clinical view template by dragging from a list of display elements or widgets as illustrated in FIG. 2a for a preferred embodiment for OCT imaging. FIG. 2a shows the screen that would be displayed when the Glaucoma follow up clinical view was selected by the user by clicking or touching on the "Glaucoma Follow Up" button 201 in the top panel of the screen. Specific views for different pathologies or disease states including but not limited to glaucoma and age related macular degeneration (AMD) may be created. Once a clinical view is selected, the display will be populated by a collection of display elements or widgets. Widgets can be related to data display or data analysis (comparison to normative data, measurements, progression analysis, from one or more instruments (OCT, Visual Field Testing, Fundus camera, etc.). In FIG. 2a, two of the displayed widgets are HFA 202, and Progression 203. Furthermore, the user can add widgets to an existing template "on the fly" by selecting from a list of categories (combo widgets, OCT, Fundus, HFA, etc.) that can be displayed somewhere on the screen. In a preferred embodiment of the invention, the user interface displays the set of widgets available at a given time which do not require additional scan information; these widgets when selected will display data instantly. If the user selects widgets that require additional patient scan information, the user interface will generate and send orders to the acquisition controls of one or more instruments for specific scans to be carried out in the future to collect the requested information. Data will be displayed when all the required scans are performed and saved on the patient record. Once a widget or display element is selected, the user has the option to populate the widget with different data. A list of available data and analysis 204 can be displayed and the user can select from the list and indicate where in the widget the data should be displayed.

Figure 2B:
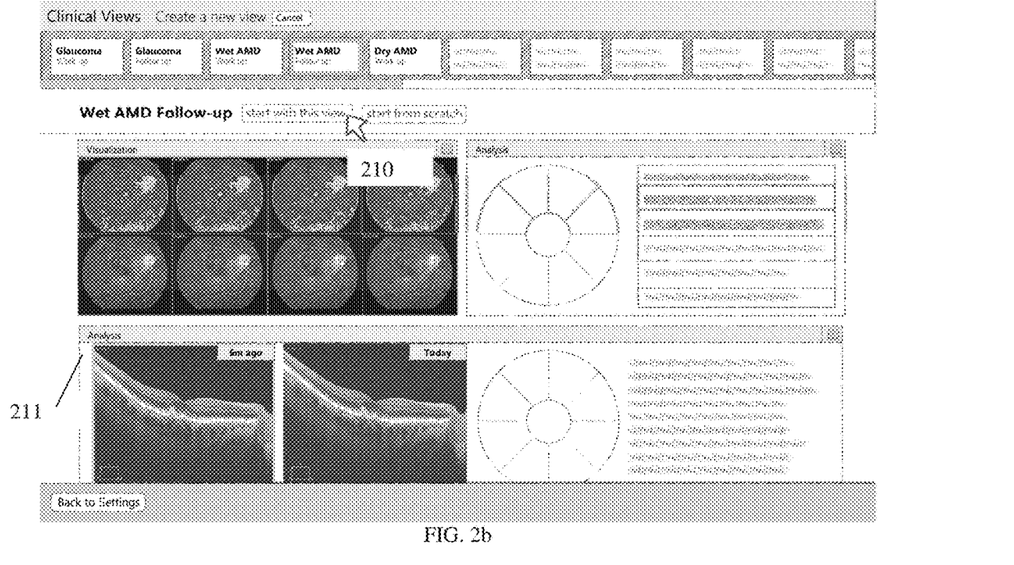
FIG. 2b shows a display when a new clinical view for Wet AMD follow-up is selected. The user is given the option to select from a pre-existing template of display elements or start from scratch.

The user also has the option to create new views from scratch using the delivered views as a template as illustrated in FIG. 2b for the Wet AMD clinical view. When the user selects "Add new view" 205 in FIG. 2a, the view shown in FIG. 2b could be displayed on the screen. The user is given the option to start with a predetermined template or start from scratch 210. Once this selection is made, the view will change to that shown in FIG. 2a where widgets relevant to the selected clinical view would be accessible via a list or menu somewhere on the screen. This list could be hidden when not in use to increase the available screen space for display of clinically meaningful data. Data from multiple visits can be displayed side by side to facilitate analysis of disease progression as shown in the Analysis panel 211 in the bottom of FIG. 2b.

Figure 3A:
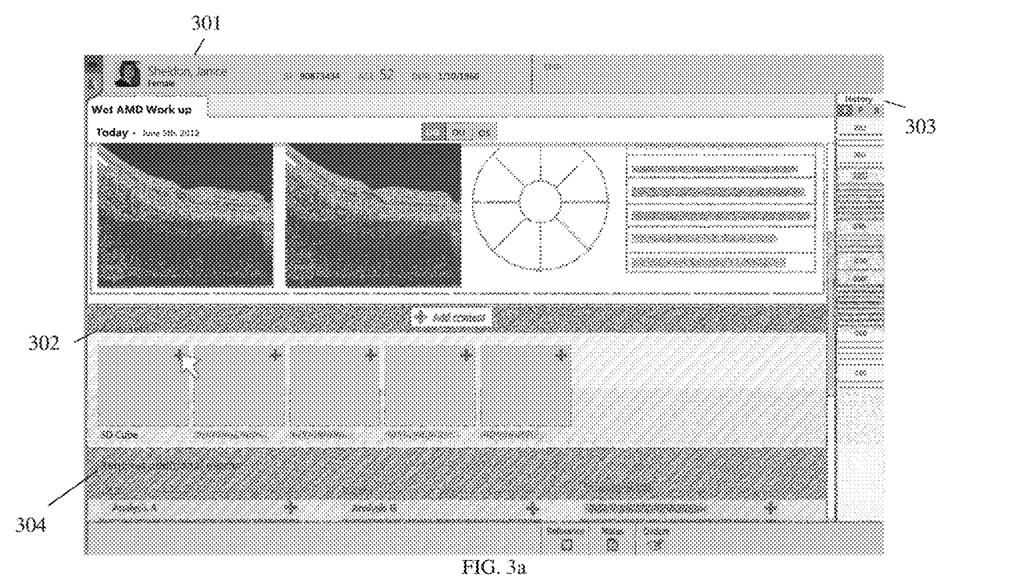
FIG. 3a shows the work-up screen for Wet AMD in which various types of analysis can be selected by the user to generate a report on a particular patient. The user is able to select from existing data as well as indicating data that should be acquired at a subsequent visit.
Figure 3B:
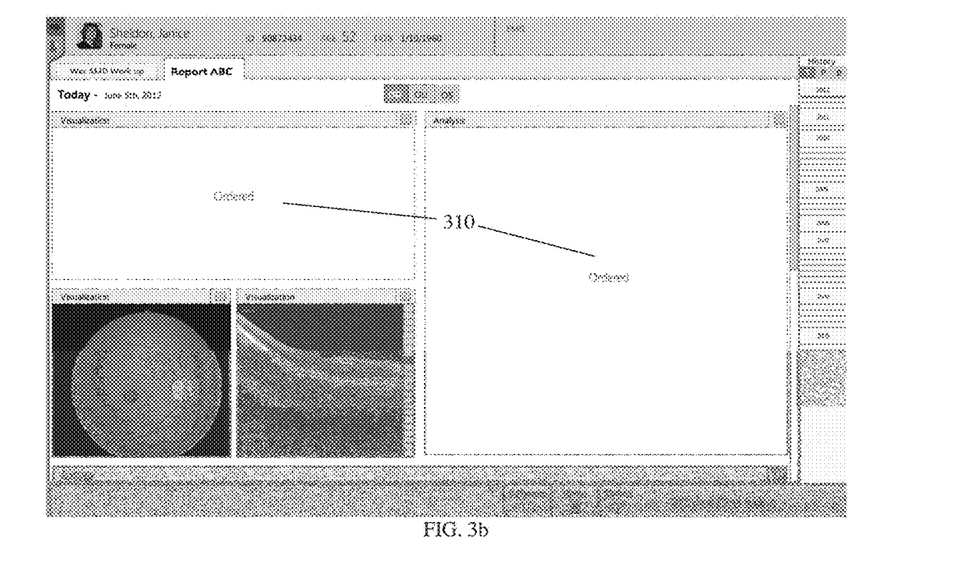
FIG. 3b shows the report generated based on the selections made from the display screen shown in FIG. 3a. Previously collected data is displayed while locations for data pending acquisition are left blank.

In a related embodiment of the present invention, the user has the option to design one or more protocols/reports either from scratch or by changing existing protocol/report templates in a similar manner to the user interface as illustrated in FIG. 3. FIG. 3a shows a "Wet AMD work up" display in which the components that can be drawn from to generate a report relevant to wet AMD can be selected by the user. Various pieces of information about the identity of the patient 301 can be included in addition to various types of ophthalmic imaging data. The user can on the fly add to an existing report additional analysis, images or scans. The set of analysis, scans and images is limited to the existing scan data if immediate display of the data is desired. This is indicated by the menu of "available" options 302 shown on the display. The user only has to select and drag the analysis option or widget that they want to add to the report from the list of available widgets on the bottom of the screen. The user can select from data collected at previous visits using a "history" display element on the screen where an indication of earlier existing data sets would be provided. The user can also select a widget or dataset and choose to view all widgets or data of the same type collected over all visits. Individual visits can be added or removed to create the progression report desired. The user can also select an analysis from which data is not presently available from the menu of "Requires additional analysis" options 304. In case, an analysis is requested that requires additional scan data, the system will automatically generate a scan order and send it to the acquisition head of the diagnostic instrument. A report generated from a selection of elements using the interface in FIG. 3a is shown in FIG. 3b. Data that has been already collected is visible. The location on the report where this data is to be displayed will remain blank or labeled "ordered" 310 until it is collected at a later date.

Protocol Driven Workflow

Figure 4A:
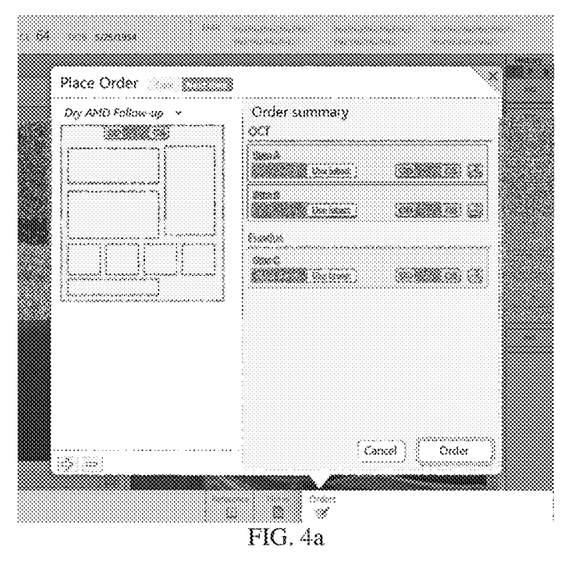
FIG. 4a illustrates a user interface screen that could be used for protocol driven workflows according to one aspect of the present invention.
Figure 4B:
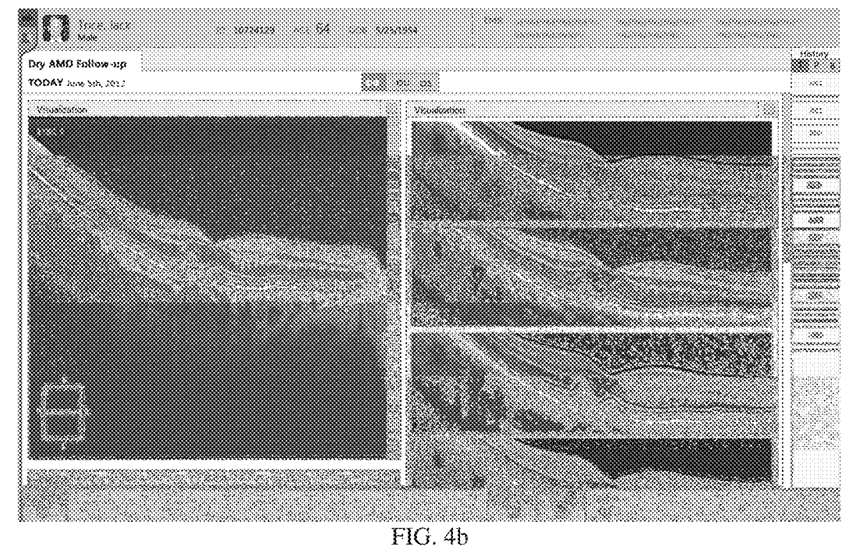
FIG. 4b displays the resulting data collected based on the workflow request.

Typically for OCT imaging, a specific scan or series of scans will be selected by the instrument user and performed on the patient based on desired information. This requires knowledge of what scan patterns are likely to provide the desired information. An aspect of the present invention is the ability for the user to order single exams, or a particular protocol which is a combination of one or more scans, or analysis from a single or multiple different diagnostic devices. This protocol driven workflow could be based on desired information on a specific disease state such as glaucoma or dry or wet AMD. This workflow also implies that the user can order the protocol for a particular patient at the end of the examination for their next visit. The information will be stored and recalled the next time the patient is examined. The user can use existing protocol templates or generate their own based on knowledge of desired information. The user can order the next visit protocol/report during the current visit. The user only has to click on the order control at the bottom of the main screen and a pop-up screen will show-up as illustrated in FIG. 4a. On this screen, the user can select which protocol to order for next visit. Either the same as current visit, a new one (based on existing templates), or order existing protocol and add additional scans to it. These orders will then be retrieving on 1 or more diagnostic acquisition devices. An example of a specific exam protocol is illustrated in FIG. 4a. Here a follow-up exam on dry AMD is desired and a pair of OCT scans as well as a fundus image is being ordered to allow for follow-up examination of a patient. FIG. 4b shows some of the data that is collected at the later visit based on the ordered examination protocol. If the user selects a new protocol, the system can determine the scans that are required to create the full data set that would be required by the standard scan presentation for that mode and create an order for acquisition of those scans.

Bookmarking B-Scans

Figure 5:
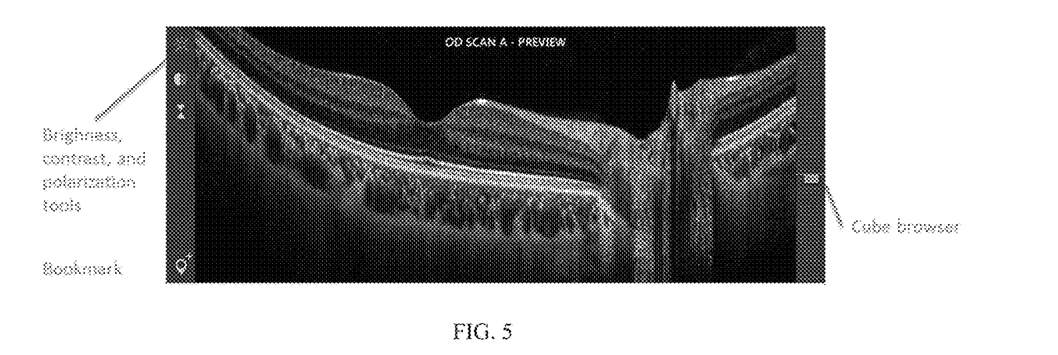
FIG. 5 shows a screen shot for an embodiment of the present invention in which particular B-scans for a cube of OCT data can be bookmarked for later reference.

The user is provided with the capability to bookmark one or more scans in a cube of data after acquisition, during review at the acquisition unit as is illustrated in FIG. 5. This function may be executed by the technician that is operating the instrument or by a doctor preparing an analysis to share with the patient, or colleagues, or a referring clinician, or as a reminder for any future reviewer. The user will select the scan that they want to highlight in the volume of data by scrolling up and down on the cube bar using any one of a number of user input devices including but not limited to a touchscreen interface, a scroll wheel, a mouse, or one or more buttons to advance forward and backward. After selecting the scan, the user will drag the bookmark icon to the scan using any user input means. This pre-screening step of bookmarking B-scans will help highlight any type of pathology or abnormality that was noted during acquisition. In addition to bookmarking, the user can annotate a particular scan with notes or measurement information and this information will be stored with the data for later recall.

Reference Library

Figure 6:
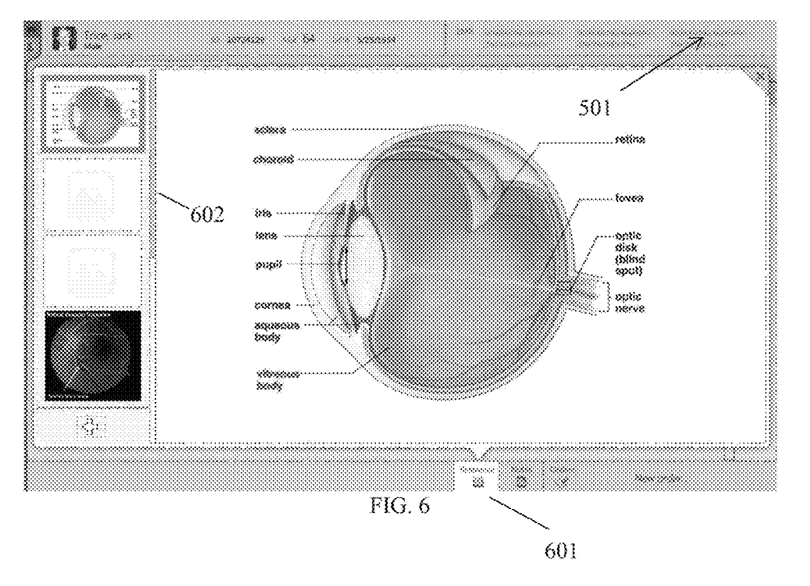
FIG. 6 shows a model of the eye that could be accessed from a reference library during acquisition, display or analysis of ophthalmic diagnostic data according to one aspect of the present invention.

In a further embodiment of the invention, the user interface allows access to a reference library with educational material pertaining to eye anatomy, healthy reference scans and examples of diseased scans that can be accessed by the user throughout acquisition and analysis of the ophthalmic diagnostic data as illustrated in FIG. 6. The user can click on the library icon 601 on the bottom of the page to access the library. A scroll bar 602 can be the navigation tool on this screen. After selecting a particular scan/image the user can toggle from standard to full screen. In addition, each of the scans/images has a control on the right upper corner to toggle between the patient scan and a health reference scan for comparison. It is also possible for doctors to add their own information to the library. The model eye can be clicked on to select a portion of the eye for which reference images are desired, such as the fovea, the optic nerve head, the arcades, the angle, or the cornea.

Click to Scan

Figure 7A:
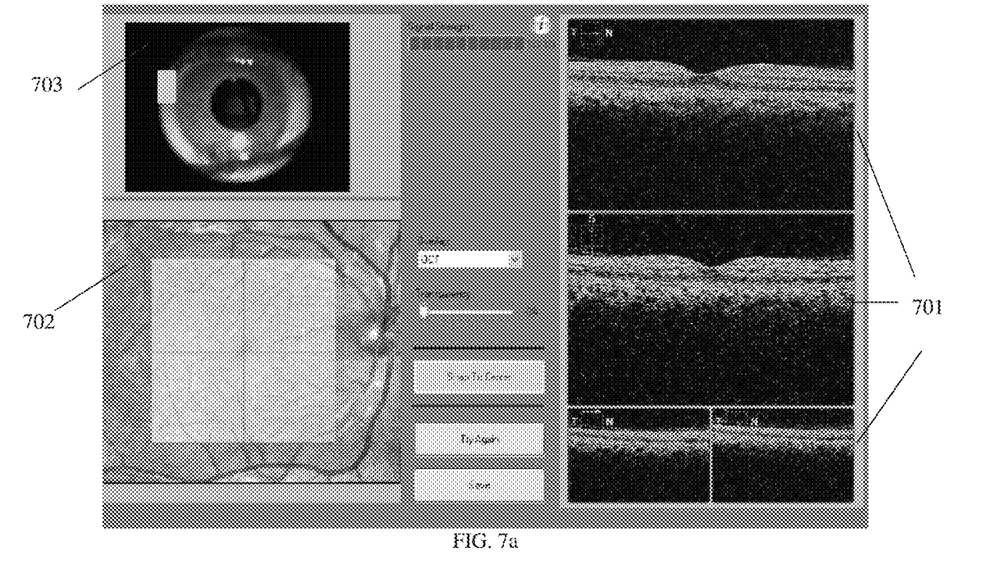
FIG. 7a illustrates a review screen in which a fundus image is displayed alongside various OCT slices.

In the past, the operator has to identify the point(s) of interest on a fundus view generated from either OCT data or a separate fundus imaging modality during alignment and use that information to guide further data acquisition. This can be challenging given the patients' motion and given the inherent differences in the visualization of structures in the OCT cross-sectional B-scan as compared to an en face fundus image which may be in color or contain functional information such as fluorescein angiography. A further embodiment of the present invention allows the instrument operator to identify the region of interest on a relatively motion free fundus image in a review screen and to take a finer or higher definition scan with patient's head still in position to be scanned. FIG. 7a illustrates a collection of data for a particular patient. The data can include low definition B-scans 701 that can be linked via color coding to locations on a view of the patient's retina or fundus 702. The fundus image could be generated from OCT data [23] or from an alternative imaging modality including but not limited to line scanning ophthalmoscope (LSO), fundus camera, confocal scanning laser ophthalmoscope (cSLO). In addition a view of the patient's iris and pupil 703 can also be displayed to indicate where the OCT beam is passing through the patient's eye.

Figure 7B:
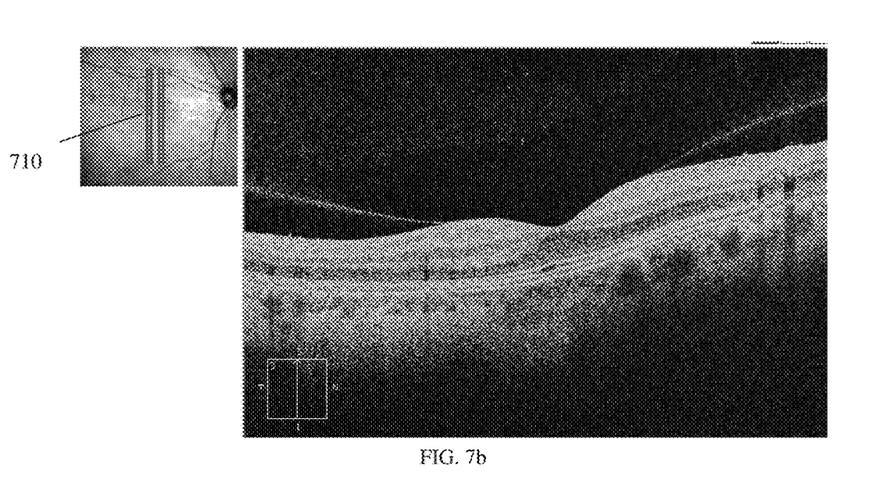
FIG. 7b displays a high quality tomogram or B-scan that can be ordered directly from the review screen shown in FIG. 7a according to one aspect of the present invention.

During the acquisition of OCT data, after taking an overview scan of the eye, the operator reviews the overall scan and specifies a region of interest on the Fundus image 702 using any one of a variety of user input devices including mouse clicks, touch screen, etc. The system can automatically identify a region of interest such as the fovea or optic disc or the user can adjust the line displayed on the fundus image to guide further data acquisition. The user can then click or select a high definition data scan using a user interface element on the display. The machine acquires a finer scan at the region of interests with a higher resolution as illustrated in FIG. 7b. The increased resolution can be obtained by collecting multiple scans at the same location and averaging or by sampling at a higher density. Details of the location of the high definition scan 710 are displayed along with the data.

In a preferred embodiment of the present invention, during the acquisition of OCT data,
1. The operator takes an overview scan of patient's eye.
2. While patients head is still in position for the next scan, the operator reviews the overview scan.
3. The operator specifies the region of interest guided by the automatically identified landmark, such as fovea, by dragging the mouse or a slice navigator.
4. The instrument takes a scan with higher resolution than that of the overview scan on the region of interest.

While the preferred embodiment involves selecting the region for additional data collection while the patient's head is still positioned in the instrument, the same idea could be applied to review of data and ordering of scans for subsequent visits. In addition, locations for additional data collection could be selected from a preliminary cube of OCT data such that any arbitrary location could be selected and scans could be collected along any arbitrary axes or directions within the cube.

Method for Virtual Real-Time Z-Tracking

In current OCT systems, as the tissue moves in the axial dimension, the position of the tissue in the OCT signal could vary significantly. Hence it is desirable to have some form of z-tracking that tries to position the tissue in each B-Scan at the optimal location. However current methods rely on finding the position of the tissue and then moving a reference mirror to adjust the position of the acquired data so that the tissue is positioned optimally. This is typically accomplished by a mechanical movement of one of the arms of the interferometer. However because of the mechanical movement (which is slow) the tissue might never be positioned optimally if there is constant motion and the algorithms are constantly trying to catch up to the tissue. This is especially undesirable if the user is taking some actions based on the OCT signal. For example, in an OCT system integrated with a surgical microscope, the physician will be taking some actions based on the signal they see on the display. Hence it is very desirable if the tissue can be displayed at an optimal location (that can be set by the user) in real-time. A further aspect of the present invention would enable real-time z-tracked display of OCT data to the user. The invention will be particularly useful for applications where it is very important to have a stabilized "view" of the OCT data being acquired. One example is OCT for ophthalmic surgery.

The main idea of the present invention is to increase the OCT imaging depth to a larger depth compared to the region of interest. For instance, if a surgeon is looking at the posterior region of the eye for surgery, he is mainly interested in 2 to 4 mm of tissue. If a larger region of tissue can be imaged, then automatic algorithms can be used to segment the tissue region in the image in real-time. The displayed region to the user can then be centered on the region of interest hence ensuring that the tissue is always positioned at the optimal location selected by the user. The main advantage of this method is that the current invention can achieve z-tracked display in real-time.

With the development of new OCT technologies, especially swept source OCT, more imaging depth will become feasible. It has been shown that imaging depths of 6 mm or more are possible with Swept Source systems. For the current discussion, we will use the example of an imaging depth of 6 mm and a region of interest of 3 mm (for imaging the posterior segment, this depth for the region of interest is usually sufficient).

Figure 8:
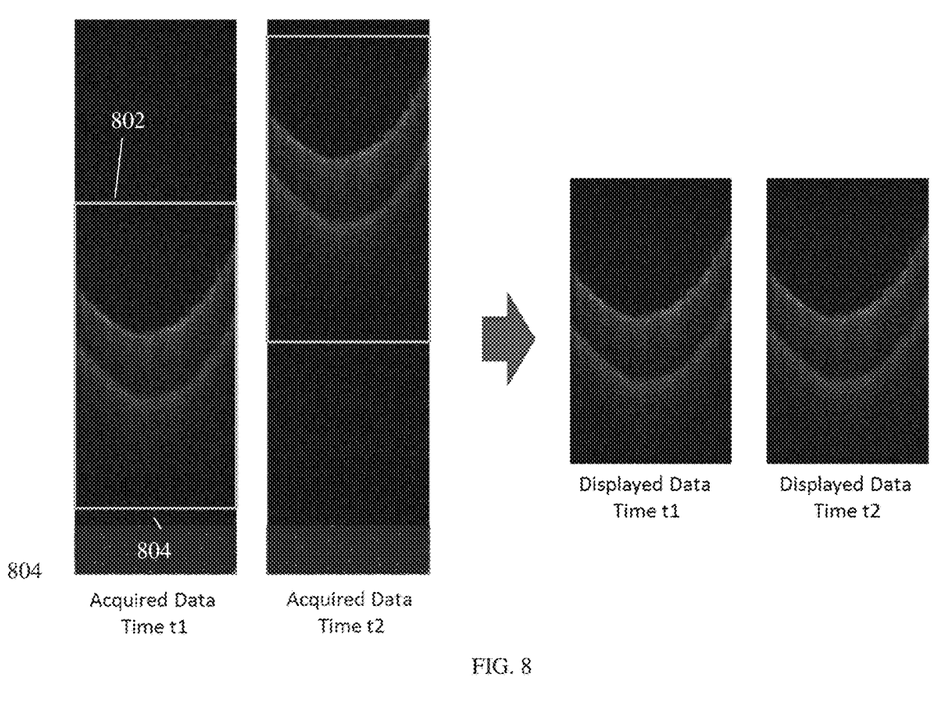
FIG. 8 illustrates the basic concept behind virtual real time z-tracking in which a reduced subset of depth information is used to maintain a constant depth view over time.

FIG. 8 shows an overview of the concept. At time t1, the data is acquired as shown on the extreme left (Ex: 6 mm imaging depth). Automatic algorithms can segment the tissue of interest and a region of interest is placed around it as shown by lines 802 and 804 (Ex: 3 mm). This region of interest is displayed to the user as shown on the first image to the right of the arrow. At time t2, the tissue has moved along the axial dimension and hence is placed at a different location on the acquired data window as shown on the second image. The tissue can be segmented again and the region of interest moved to match the tissue region of interest. The displayed image at time t2 has the tissue placed at the same location as in the displayed image at time t1. Since the segmentation algorithm can be very fast, the display can be achieved in real time and presents the user with a virtual real-time z-tracking capability.

It should be noted that the depth of the region of interest is not a limitation. If the automatic algorithms determine that the tissue being imaged is thicker than the currently set region of interest, then the region of interest itself can be expanded to contain the tissue of interest. The only limitation will be the imaging depth that is possible with the instrument under consideration. If the tissue goes out of even the extended region of the scan, then traditional methods of moving the reference mirror might be needed to bring the tissue back into range.

The tissue region can be segmented from the OCT B-Scan using very fast thresholding algorithms. Since we are mainly interested in finding the region of interest, the segmentation algorithms need not be precise. A rough segmentation of the tissue will be sufficient to center the region of interest. Further, the data can be down-sampled as needed to increase the speed of detection. Thresholding approaches are just one way to provide segmentation. Additional ways to segment the data can be envisioned by those skilled in the art.

Improved Contrast and Visual Quality of Averaged B-Scans Using a Single Control Parameter Typically, the user is provided with brightness and contrast (B,C) settings which they can vary to come up which an optimal setting for display of a particular piece of OCT data. This is a two dimensional exhaustive search within a pair of parameters that can vary within a large range. A further aspect of the present invention provides the user with just one parameter which varies between 0 and 1 to control the quality of the display, and hence is easy to understand, set, and interpret.

After averaging a group of registered B-scans to improve Signal-to-Noise (SNR), the proposed method calculates a global, single value from the data, and removes a fraction of it from the averaged data, resulting in a B-scan that shows significant improvements in intra-layer contrast, visibility of detail, and object-to-background contrast. The primary application for this method is to improve the image quality of averaged B-scans. In alternative embodiment, it can be used to provide a reduced control parameter set (n=1) to the user for setting the intensity level of the image that provides better contrast. The parameter could be displayed and adjusted by the user without detailed knowledge of the specific optimization process.

Figure 9A:
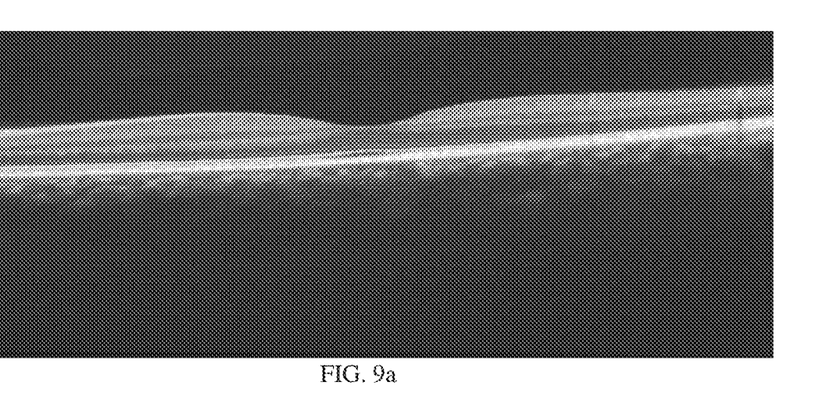
FIG. 9a shows an OCT B-scan in which 64 B-scans were registered and averaged.

FIG. 9a shows the result of an averaging process, where a stack of 64 frames, scanned at roughly the same anatomical location were co-registered, and a median intensity value was obtained at each pixel location. In a preferred embodiment of the proposed method, first a mean of these median values that make up the image at this stage is calculated. Let us denote the median image by m, and the mean by <m>. The contrast enhancement is then obtained by subtracting a fraction of this <m> from m, for example according to:

$$m' \text{ (improved)} = m - (\text{alpha})<m> \quad (1)$$

Figure 9B:
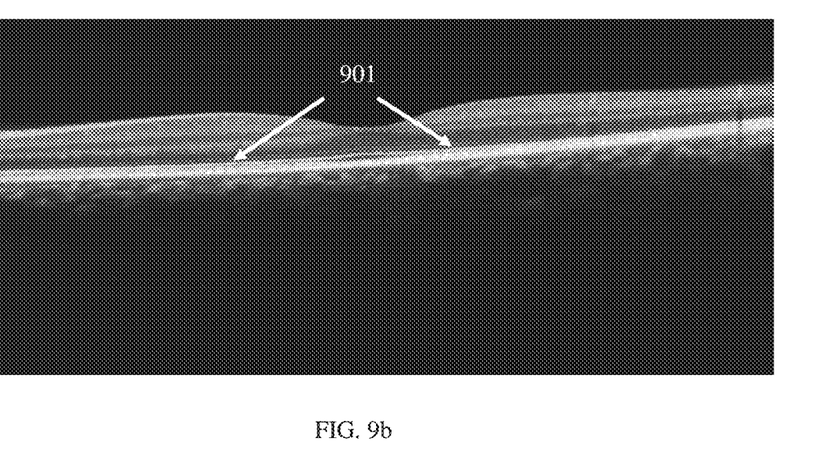
FIG. 9b shows a contrast enhanced version of the image in FIG. 9a according to one aspect of the present invention.

An example of the improved image is shown in FIG. 9b, where the interlayer contrast has increased, while still preserving the details from the vitreous to the outer extent of the choroid. The value of alpha, that was subjectively determined to provide both a contrast enhancement and preservation of detail, is 0.58 in FIG. 9b. Also worth noticing is that because of this modification induced in the original image by a single control parameter (equation 1 above), the visibility of fine layers like the IS/OS boundary (arrows 901) is significantly increased.

User Generated Normative Databases

Current commercially available OCT systems such as Cirrus HD-OCT (Carl Zeiss Meditec, Inc. Dublin, Calif.) provide the opportunity for doctors to compare a particular patient to a collection of normative data for analysis and disease diagnosis. Companies such as Carl Zeiss attempt to provide a collection of data that will apply to a broad patient population. In some cases, doctors want to compare their patients with their local normal population either because of ethnic variations or variations due to specific disease conditions. Clinicians are typically imaging numerous patients for their own studies and want to use their own patient population as the reference.

It is a further aspect of the present invention to enable users to generate reference databases of their own, and to compare patients with this reference databases. The deviation from the User Generated Reference database can be visualized in the similar fashion of the deviation from Normative Database. In a further embodiment, users can adjust the threshold of deviations to provide meaningful comparisons depending on the normative data. In addition, the user interface will allow doctors to export and import their customized reference databases to allow for sharing between practitioners.

Although various applications and embodiments that incorporate the teachings of the present invention have been shown and described in detail herein, those skilled in the art can readily devise other varied embodiments that still incorporate these teachings.

The following references are hereby incorporated by reference:

1. Ajtony C, Balla Z, Somoskeoy S, Kovacs B: Relationship between Visual Field Sensitivity and Retinal Nerve Fiber Layer Thickness as Measured by Optical Coherence Tomography. *Investigative Ophthalmology & Visual Science* 2007, 48(1):258-263.
2. Sommer A, Katz J, Quigley H A, Miller N R, Robin A L, Richter R C, Witt K A: Clinically detectable nerve fiber atrophy precedes the onset of glaucomatous field loss. *Arch Ophthalmol* 1991, 109(1):77-83.
3. Sato S, Hirooka K, Baba T, Yano I, Shiraga F: Correlation between retinal nerve fibre layer thickness and retinal sensitivity. *Acta Ophthalmologica* 2008, 86(6): 609-613.
4. Harwerth R S, Wheat J L, Fredette M J, Anderson D R: Linking structure and function in glaucoma. *Progress in retinal and eye research* 2010, 29(4):249-271.
5. Gardiner S K, Johnson C A, Cioffi G A: Evaluation of the Structure-Function Relationship in Glaucoma. *Investigative Ophthalmology & Visual Science* 2005, 46(10):3712-3717.

6. Chang R, Budenz D L: New developments in optical coherence tomography for glaucoma. *Curr Opin Ophthalmol* 2008, 19(2):127-135.
7. Schuman J S, Pedut-Kloizman T, Hertzmark E, Hee M R, Wilkins J R, Coker J G, Puliafito C A, Fujimoto J G, Swanson E A: Reproducibility of nerve fiber layer thickness measurements using optical coherence tomography. *Ophthalmology* 1996, 103(11):1889-1898.
8. Paunescu L A, Schuman J S, Price L L, Stark P C, Beaton S, Ishikawa H, Wollstein G, Fujimoto J G: Reproducibility of nerve fiber thickness, macular thickness, and optic nerve head measurements using StratusOCT. *Invest Ophthalmol Vis Sci* 2004, 45(6):1716-1724.
9. Budenz D L, Chang R T, Huang X, Knighton R W, Tielsch J M: Reproducibility of retinal nerve fiber thickness measurements using the stratus OCT in normal and glaucomatous eyes. *Invest Ophthalmol Vis Sci* 2005, 46(7):2440-2443.
10. Bengtsson B, Olsson J, Heijl A, Rootzén H: A new generation of algorithms for computerized threshold perimetry, SITA. *Acta Ophthalmologica Scandinavica* 1997, 75(4):368-375.
11. Budenz D L, Michael A, Chang R T, McSoley J, Katz J: Sensitivity and specificity of the StratusOCT for perimetric glaucoma. *Ophthalmology* 2005, 112(1):3-9.
12. Hougaard J L, Heijl A, Bengtsson B: Glaucoma detection by Stratus OCT. *J Glaucoma* 2007, 16(3): 302-306.
13. Leung C K, Chong K K, Chan W M, Yiu CK, Tso M Y, Woo J, Tsang M K, Tse K K, Yung W H: Comparative study of retinal nerve fiber layer measurement by StratusOCT and GDx VCC, II: structure/function regression analysis in glaucoma. *Invest Ophthalmol Vis Sci* 2005, 46(10):3702-3711.
14. El Beltagi T A, Bowd C, Boden C, Amini P, Sample P A, Zangwill L M, Weinreb R N: Retinal nerve fiber layer thickness measured with optical coherence tomography is related to visual function in glaucomatous eyes. *Ophthalmology* 2003, 110(11):2185-2191.
15. Huang et al. "Optical Coherence Tomography" Science 254(5035):1178 1991
16. U.S. Pat. No. 5,321,501
17. Nassif et al. "In vivo human retinal imaging by ultrahigh-speed spectral domain optical coherence tomography" Optics Letters 29(5):480 2004
18. Choma, M. A., et al. "Sensitivity advantage of swept source and Fourier domain optical coherence tomography" Optics Express 11(18): 2183 2003
19. Wojtkowski, et al., "Three-dimensional retinal imaging with high-speed ultrahigh-resolution optical coherence tomography," *Ophthalmology* 112(10):1734 2005
20. Lee et al. "In vivo optical frequency domain imaging of human retina and choroid," *Optics Express* 14(10): 4403 2006
21. Leitgeb et al. "Ultrahigh resolution Fourier domain optical coherence tomography," Optics Express 12(10): 2156 (2004)
22. US Patent Publication No. 2008/0100612.
23. U.S. Pat. No. 7,301,644.

What is claimed is:

1. A graphical user interface (GUI) for use with optical coherence tomography (OCT) 3D volume data, said interface comprising:
   a window for selectively displaying a 2D image slice of the 3D volume data; and
   a user-selectable, control-input GUI element, wherein in response to user selection of the control-input GUI element, the 2D image slice currently displayed in the window is bookmarked for future retrieval.

2. A GUI as recited in claim 1, further comprising means for the user to annotate a specific 2D image slice with notes or measurements, wherein the annotations are also stored with the data for future retrieval.

3. The graphical user interface (GUI) of claim 1, wherein the 2D image slice is based on a B-scan, and the 3D volume data is comprised of a plurality of B-scans.

4. The graphical user interface (GUI) of claim 1, wherein the window is a review window for reviewing previously acquired volume data.

5. The graphical user interface (GUI) of claim 1, wherein the control-input GUI element is an icon.

6. The graphical user interface (GUI) of claim 5, wherein the selection of the control-input GUI element is operative to place the icon onto the currently displayed 2D image slice.

7. The graphical user interface (GUI) of claim 1, wherein the window frames the currently displayed 2D image slice, the GUI interface further comprising:
   a scroll bar proximate to the window, the scroll bar being effective for selecting a 2D image slice from the 3D volume data for display in the window.

8. The graphical user interface (GUI) of claim 7, wherein the scroll bar has a plurality of hatch marks distributed along its length, with one hatch mark highlighted to indicate the currently displayed 2D image slice.

* * * * *

UNITED STATES PATENT AND TRADEMARK OFFICE
CERTIFICATE OF CORRECTION

PATENT NO. : 10,595,720 B2
APPLICATION NO. : 15/880147
DATED : March 24, 2020
INVENTOR(S) : Melissa R. Horne et al.

It is certified that error appears in the above-identified patent and that said Letters Patent is hereby corrected as shown below:

On the Title Page

On the page 3, in Column 2, under item (56) "Other Publications", Line 3, delete "Investigatative" and insert -- Investigative --, therefor.

On the page 3, in Column 2, under item (56) "Other Publications", Line 41, delete "Opthalmoscopy," and insert -- Ophthalmoscopy, --, therefor.

In the Specification

In Column 11, Line 44, delete "1991" and insert -- 1991. --, therefor.

In Column 11, Line 45, delete "5,321,501" and insert -- 5,321,501. --, therefor.

In Column 11, Line 48, delete "2004" and insert -- 2004. --, therefor.

In Column 11, Line 51, delete "2003" and insert -- 2003. --, therefor.

In Column 12, Line 3, delete "2005" and insert -- 2005. --, therefor.

In Column 12, Line 6, delete "2006" and insert -- 2006. --, therefor.

In Column 12, Line 9, delete "(2004)" and insert -- (2004). --, therefor.

Signed and Sealed this
Nineteenth Day of November, 2024

Katherine Kelly Vidal
*Director of the United States Patent and Trademark Office*